US009867666B2

(12) United States Patent
Galli

(10) Patent No.: US 9,867,666 B2
(45) Date of Patent: *Jan. 16, 2018

(54) DEVICE AND METHOD FOR THE TREATMENT OF THE VAGINAL CANAL AND RELEVANT EQUIPMENT

(71) Applicant: EL. EN. S.P.A., Calenzano (IT)

(72) Inventor: Mauro Galli, Sesto Fiorentino (IT)

(73) Assignee: EL. EN. S.P.A., Calenzano, (FI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/062,584

(22) Filed: Mar. 7, 2016

(65) Prior Publication Data

US 2016/0184015 A1 Jun. 30, 2016

Related U.S. Application Data

(63) Continuation of application No. 13/577,133, filed as application No. PCT/IT2011/000023 on Jan. 28, 2011, now abandoned.

(30) Foreign Application Priority Data

Feb. 4, 2010 (IT) ................................. FI2010A0015

(51) Int. Cl.
| | |
|---|---|
| *A61B 18/22* | (2006.01) |
| *A61B 18/20* | (2006.01) |
| *A61N 5/067* | (2006.01) |
| *A61N 5/06* | (2006.01) |
| *A61B 17/42* | (2006.01) |
| *A61B 1/303* | (2006.01) |

(52) U.S. Cl.
CPC ............ *A61B 18/201* (2013.01); *A61B 17/42* (2013.01); *A61B 1/303* (2013.01); *A61B 2018/20359* (2017.05); *A61B 2218/008* (2013.01); *A61N 5/06* (2013.01)

(58) Field of Classification Search
None
See application file for complete search history.

(56) References Cited

U.S. PATENT DOCUMENTS

| | | | | |
|---|---|---|---|---|
| 5,246,437 A | * | 9/1993 | Abela ..................... | A61B 18/24 604/20 |
| 5,342,358 A | * | 8/1994 | Daikuzono ............ | A61B 18/28 606/15 |
| 5,582,752 A | | 12/1996 | Zair | |
| 6,463,331 B1 | * | 10/2002 | Edwards ............ | A61B 18/1477 606/29 |

(Continued)

FOREIGN PATENT DOCUMENTS

| | | | |
|---|---|---|---|
| WO | 03/013653 A1 | 2/2003 | |
| WO | WO 2012092508 A2 * | 7/2012 | ............. A61B 18/22 |

OTHER PUBLICATIONS

Lumenis Group of companies, CO2 Laser Accessories, 2008.*

(Continued)

*Primary Examiner* — Lynsey Eiseman
*Assistant Examiner* — Manolis Pahakis
(74) *Attorney, Agent, or Firm* — McGlew and Tuttle, P.C.

(57) ABSTRACT

A device and method for the treatment of the vaginal canal by a laser beam, includes a vaginal canal wall retractor, associated to a system for directing the laser beam towards a wall of the vaginal canal.

6 Claims, 1 Drawing Sheet

(56) References Cited

U.S. PATENT DOCUMENTS

| | | | | |
|---|---|---|---|---|
| 6,565,561 B1* | 5/2003 | Goble | A61B 18/148 | 606/41 |
| 6,697,666 B1* | 2/2004 | Richards-Kortum | A61B 5/0071 | 600/478 |
| 6,818,903 B2* | 11/2004 | Schomacker | A61B 5/0059 | 250/458.1 |
| 8,961,577 B2* | 2/2015 | Reil | A61N 5/0616 | 607/88 |
| 2002/0138071 A1 | 9/2002 | Angeley et al. | | |
| 2003/0028180 A1* | 2/2003 | Franco | A61B 18/20 | 606/14 |
| 2003/0232303 A1* | 12/2003 | Black | A61N 5/0603 | 433/29 |
| 2005/0049582 A1* | 3/2005 | DeBenedictis | A61B 18/20 | 606/9 |
| 2005/0251116 A1* | 11/2005 | Steinke | A61B 5/0066 | 606/8 |
| 2005/0259933 A1* | 11/2005 | Temelkuran | A61B 1/018 | 385/123 |
| 2005/0259942 A1* | 11/2005 | Temelkuran | A61B 18/201 | 385/147 |
| 2006/0167531 A1* | 7/2006 | Gertner | A61N 5/0603 | 607/86 |
| 2006/0183072 A1* | 8/2006 | Black | A61H 7/005 | 433/29 |
| 2006/0189972 A1* | 8/2006 | Grossman | A61B 18/1477 | 606/32 |
| 2006/0217695 A1* | 9/2006 | DeBenedictis | A61B 18/201 | 606/18 |
| 2007/0162092 A1* | 7/2007 | Yen | A61N 5/0603 | 607/89 |
| 2007/0233191 A1* | 10/2007 | Parmer | A61B 18/1485 | 607/1 |
| 2008/0031924 A1* | 2/2008 | Gilson | A61N 5/0616 | 424/433 |
| 2008/0065003 A1* | 3/2008 | Neuberger | A61N 5/0601 | 604/21 |
| 2008/0132886 A1* | 6/2008 | Cohen | A61B 18/203 | 606/34 |
| 2008/0294150 A1* | 11/2008 | Altshuler | A61B 18/203 | 606/3 |
| 2009/0216219 A1* | 8/2009 | Venter | A61N 5/0616 | 606/11 |
| 2009/0319008 A1* | 12/2009 | Mayer | A61N 5/0603 | 607/90 |
| 2010/0004644 A1* | 1/2010 | Zipper | A61B 18/1402 | 606/14 |
| 2010/0100160 A1* | 4/2010 | Edman | A61B 5/0059 | 607/88 |
| 2010/0286576 A1* | 11/2010 | Pryor | A61H 21/00 | 601/18 |
| 2011/0004203 A1* | 1/2011 | Zipper | A61B 18/1402 | 606/15 |
| 2011/0178584 A1* | 7/2011 | Parmer | A61B 90/06 | 607/102 |
| 2012/0179229 A1* | 7/2012 | Tettamanti | A61N 5/0603 | 607/89 |
| 2014/0148878 A1* | 5/2014 | Khatri | A61N 5/0603 | 607/89 |
| 2015/0265387 A1* | 9/2015 | Alexander | A61B 17/3468 | 600/37 |
| 2016/0059034 A1* | 3/2016 | Kiang | A61N 5/0603 | 607/92 |
| 2016/0158573 A1* | 6/2016 | Masotti | A61B 1/303 | 600/407 |
| 2016/0346568 A1* | 12/2016 | Rockweiler | A61B 5/01 | |

OTHER PUBLICATIONS

Lumenis group of companies, ULTRAPulse SurgiTouch, 2008.*
McBride et al., Vulvovaginal Atrophy, Mayo Clin Proc. 2010;85(1):87-94.*
European Office Action dated Oct. 13, 2015.

* cited by examiner

DEVICE AND METHOD FOR THE TREATMENT OF THE VAGINAL CANAL AND RELEVANT EQUIPMENT

CROSS REFERENCE TO RELATED APPLICATIONS

This application is a continuation under 37 CFR 1.53(b) of pending prior application Ser. No. 13/577,133 filed Aug. 3, 2012 and claims the benefit (35 U.S.C. §120 and 365(c)) of International Application PCT/IT2011/000023 filed Jan. 28, 2011 and claims the benefit of priority under 35 U.S.C. § 119 of Italian Patent Application FI2010A000015 filed Feb. 4, 2010, the entire contents of each application are incorporated herein by reference.

FIELD OF THE INVENTION

The present invention relates to the field of electro-medical machines, and more in particular the field of machines and equipment using a laser source for treating the human body.

BACKGROUND OF THE INVENTION

Multiple applications of laser radiation are known for surgical, aesthetic or therapeutic treatment of the human body. In some applications, laser is used as a cutting instrument in replacement of scalpels. In other applications, laser is used for causing the necrosis of neoplastic tissues, for the bio-stimulation of the growth of particular types of tissues, for example of the cartilaginous tissue, for pain treatment. In applications more strictly related to aesthetic treatments, laser radiation is used for wrinkle reduction, skin rejuvenation, hair scalp treatment for favoring hair growth, stimulation of collagen production, etc.

SUMMARY OF THE INVENTION

The object of the invention is a new use of laser radiation in the medical field, and equipment as well as a device specifically designed and made for such new application.

In substance, according to a first aspect thereof, the invention provides a device for treating the-vaginal canal by a laser beam, comprising a vaginal canal wall retractor, associated to a system for directing the laser beam towards the wall. This allows using the laser beam for treating the mucosa of the vaginal canal. The main purpose of the treatment that may be performed with the device according to the invention is to prevent and treat atrophic vaginitis, a condition typical but not exclusive of the post-menopause period that currently is normally treated with estrogens for short periods. Atrophic vaginitis is a pathological condition characterized by an inflammation of the vaginal mucosa with progressive decrease of the mucosa thickness due to the loss of collagen structure. Atrophic vaginitis is a highly disabling condition responsible for considerable psychological discomfort for women suffering from this condition, due to the associated pain, burn, bleeding, ectropion and due to the impossibility of having normal sexual intercourse (dyspareunia).

According to the invention, vice versa, atrophic vaginitis is prevented or treated by impinging the mucosa that covers the vaginal canal through a preferably pulsed laser beam of suitable wavelength and power, which allows renewing the epithelium, that is, the mucosa surface layer which, in addition, acts on the underlying plate, stimulating the production of collagen.

According to some embodiments, the system for directing, that is, orientating the laser beam comprises a mirror advantageously arranged within an empty volume defined by expansion members that interact with the vaginal canal, causing the expansion thereof upon the introduction of the device into the vagina.

The beam directing mirror may be mobile, but in a preferred embodiment of the invention it is arranged in a fixed position within the hollow volume defined by the expansion members, in the proximity of the distal end of said volume, that is, the one that upon the introduction of the device into the vagina is the innermost in the treated organ.

The expansion members may consist of a frame of longitudinal bent metal elements, for example brackets bent as a U. For better comfort during treatment and for an easier introduction of the device, it is possible to provide for the expansion members to be contained within a skirt or protection wall that at least partly covers said frame, leaving a window or aperture for the laser exit. In some embodiments it is possible to provide for the skirt or protection wall to be integrally or at least partly made of a material transparent to the laser radiation. In this way it is not necessary to provide an opening in the skirt at the point wherein the laser exits.

The treatment is simply performed by introducing the device into the vaginal canal, causing the widening of the vaginal canal by means of the retracting members, rotating it about the device axis and moving it in the introduction and removal direction, so as to impinge the entire vaginal canal, or the part thereof that requires treatment, with the laser beam.

In some embodiments, the device may comprise a scanning system whereto the retractor may advantageously be coupled in a reversible manner, so as to allow for example the sterilization of the retractor or the use of disposable retractors. The laser beam scanning system is advantageously arranged and controlled for directing a laser beam on the beam directing system, housed in the part of the device that is introduced into the vaginal canal, and for moving the beam according to a presettable path so as to perform a spot treatment on each treated portion of the mucosa for each position the operator places the device into the vaginal canal.

In some embodiments, the scanning system comprises a mirror or a pair of mirrors with galvanometer means that control the oscillation about two axes orthogonal to one another, under the control of a programmable control unit. The latter may be programmed for making the mirrors, and thus the laser beam, do predetermined movements, following a particular pattern or path defined by discrete points, spaced or not spaced from one another, whereat the laser beam interacts with the vaginal canal tissue.

In some embodiments there may be provided a suction system on the device for the fumes that generate within the vaginal canal during treatment.

According to a different aspect, the invention relates to a laser apparatus comprising a laser source, a waveguide and a device of the type described above whereto the laser beam generated by the source is conveyed through the waveguide.

In some advantageous embodiments, the laser source is a pulsed source, for example with pulses with an emission lasting between 0.1 and 10 milliseconds and preferably between 0.2 and 2 milliseconds, or a continuous source with emission times between 0.5 and 50 milliseconds. The laser radiation may have a wavelength comprised for example between 1,000 nm and 12,000 nm, preferably it may be equal to 10,600 nm.

The power of the beam emitted by the source is selected so that the beam has the effect of epithelium renewal and stimulation of collagen production on the mucosa, as mentioned above. Typically, the power may be comprised between 2 and 100 W, preferably between 10 and 50 W.

The apparatus may comprise systems for controlling the scanning mirrors, so as to move the pulsed or continuous beam for performing a treatment according to a process that provides for impinging the mucosa with laser pulses in zones or points adjacent to one another and consecutive along a predetermined path, wherein the spacing between the scanning points may preferably be comprised between 0 and 5,000 micrometers, and preferably between 50 and 5,000 micrometers and even more preferably between 200 and 2,000 micrometers.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
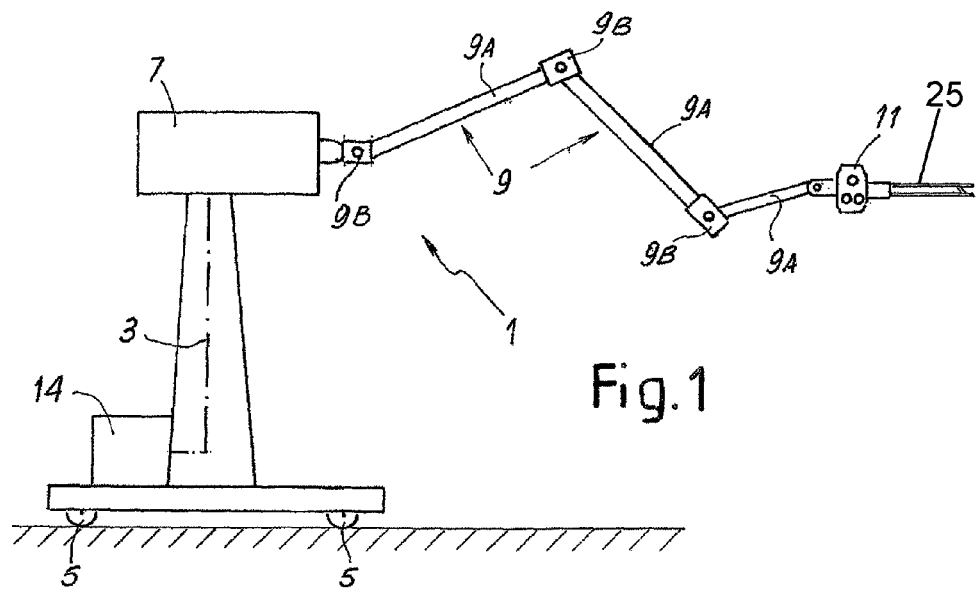
FIG. 1 is a view of an overall diagram of the apparatus.

Referring to the drawings, FIG. 1 schematically shows an apparatus according to the invention. The apparatus, indicated as a whole with reference numeral 1, has a support 3, for example fitted with wheels 5 for being moved on the floor. A laser source 7, which is connected to a treatment device 11 through a waveguide 9, is positioned on the support 3. In some embodiments, the waveguide 9 is formed by tubular segments 9A, connected to one another by articulation elements 9B, known per se, for allowing the positioning and movement of the device 11.

Figure 2:
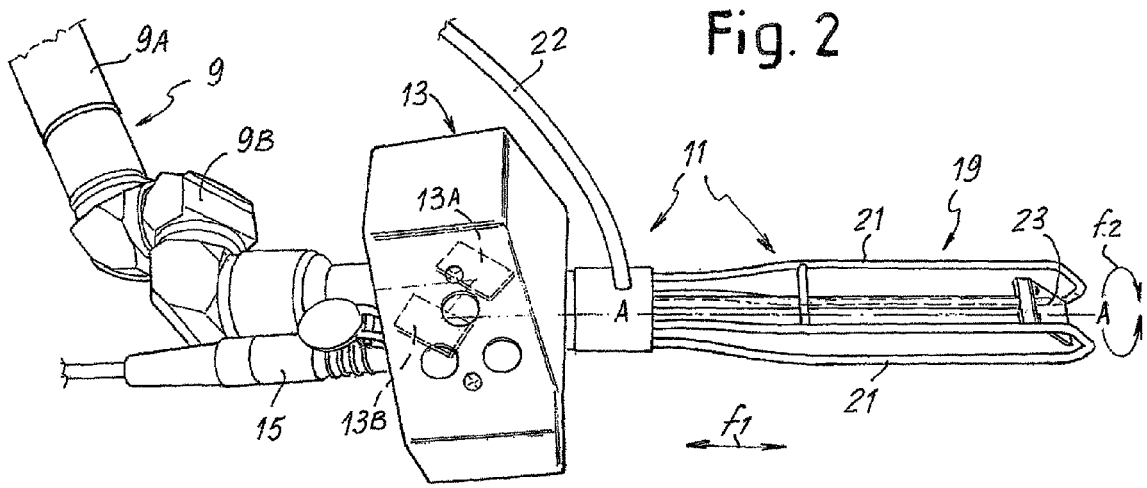
FIG. 2 is a view of a detail of the end portion of the waveguide and of the device in a possible embodiment.

The device 11 is shown in greater detail in FIG. 2. It comprises a box-shaped body forming a housing 13, wherein one or two scanning mirrors are housed. The illustrated example schematically shows with a broken line two scanning mirrors 13A and 13B. The movement of the mirrors about their oscillation axes is controlled by respective actuators, for example consisting of galvanometers, under the control of a central unit 14, for example arranged on the support 3 and connected through wiring 15 to device 11. The control unit 14 is also connected to the laser source 7 for controlling the emission of the latter. Buttons, capacitive sensors or other interface elements may be arranged on the box-shaped body forming the housing 13, allowing the operator to maneuver the device and control the laser emission.

The housing 13 of the device 11 is associated to a retractor globally indicated with 19, advantageously reversibly applicable to the housing 13 so as to use retractors 19 differing by shape and size and/or for allowing the sterilization or the use of disposable retractors 19, for clear hygiene and asepsis reasons.

In some embodiments, the retractor 19 comprises elongated linear elements 21 that form a sort of frame defining a hollow volume therein wherein there is housed a system for directing the laser beam coming from the scanning system housed in housing 13. In the embodiment shown, the system for directing the beam comprises a mirror 23 inclined to about 45° relative to the longitudinal axis indicated with A-A of the frame formed by the linear elements 21. This frame may be coated with a skirt 25 (see FIG. 1), for example made of a plastic material for favoring the introduction thereof into the vaginal canal and increasing the patient's comfort.

Introducing retractor 19 into the vaginal canal, mirror 23 takes on such position that the beam coming from the scanning system 13A, 13B is directed approximately orthogonally relative to axis A-A of the retractor, and therefore about orthogonally to a portion of the vaginal canal wall.

Moving the retractor according to arrow f1 in a direction parallel to axis A-A and rotating it according to arrow f2 about axis A-A it is possible for the operator to treat adjacent and consecutive portions of the vaginal canal through the laser beam. The latter preferably is a pulsed beam and holding mirror 23 still, each pulse is directed to a point defined by the scanning mirrors 13A and 13B. Holding device 11 in a fixed position into the vaginal canal for a certain time, the device will send a series of pulses that will affect adjacent points arranged according to a pattern or path that may be preset through the programmable control unit 14, for treating the entire zone reachable by holding mirror 23 in a predetermined position. Once this treatment is over, retractor 19 is moved angularly for impinging in a similar manner all the tissue portions that are at a certain depth into the vaginal canal. Once this treatment is over, retractor 19 is moved according to arrow 12 inwards or outwards (according to where the treatment has started), for repeating the operation on adjacent annular areas of the entire vaginal canal or in any case of the zones to be subject to treatment.

While specific embodiments of the invention have been shown and described in detail to illustrate the application of the principles of the invention, it will be understood that the invention may be embodied otherwise without departing from such principles.

What is claimed is:

1. A method of treating atrophic vaginitis, the method comprising:

providing a laser source, said laser source emitting a laser beam;

providing a device connected to the laser source, said device comprising a vaginal canal wall retractor having a longitudinal axis and a laser beam scanning system, said vaginal canal wall retractor is detachable from the laser scanning system and comprises spaced apart bars extending in the longitudinal axis and defining between them a hollow volume and an aperture, said laser beam scanning system being arranged and configured for receiving the laser beam from the laser source and directing said laser beam on a mirror arranged in the hollow volume, said mirror being arranged in a fixed position within said hollow volume at a distal part of said hollow volume;

introducing the vaginal canal wall retractor in a vaginal canal of a patient having atrophic vaginitis;

moving said laser beam according to a pre-settable treatment pattern via said laser beam scanning system;
directing the moving laser beam towards the mirror;
reflecting the laser beam by means of said mirror transversely to the longitudinal axis of the wall retractor through said aperture toward mucosa of a lateral surface of the vaginal canal, and applying the laser beam in points having a spacing of 5,000 micrometers or less along a predetermined path of the mucosa, the laser beam having a power of 2 to 100 W, a wavelength between 1,000 nanometers and 12,000 nanometers, and being pulsed with a pulse duration between 0.1 and 10 milliseconds or continuous with an emission duration between 0.5 and 50 milliseconds, to induce renewal of the mucosa and stimulate collagen production under the mucosa.

2. The method of claim 1, wherein the laser beam scanning system moves the laser beam such that the laser beam reflected by said mirror engages the mucosa of the vaginal canal along sequentially arranged adjacent zones along said pre-settable treatment pattern.

3. The method of claim 1, further comprising the following steps:
  a) positioning the vaginal canal wall retractor in the vaginal canal and moving the laser by means of the laser beam scanning system according to the pre-settable treatment pattern and reflecting the moving laser beam towards a first portion of the mucosa of the vaginal canal by means of said mirror when the vaginal canal wall retractor is positioned in the vaginal canal;
  b) moving the vaginal canal wall retractor and the mirror arranged therein in a different position within the vaginal canal when the pre-settable treatment pattern is completed;
  c) repeating step (a) to treat a different portion of the vaginal canal.

4. The method of claim 1, further comprising the step of causing renewing of mucosa epithelium and stimulation of collagen production in the vaginal mucosa via said laser beam.

5. The method of claim 1, wherein a length of each side of the vaginal canal wall retractor is free of structure such that the laser beam passes directly from the mirror to the vaginal canal.

6. The method of claim 1, wherein each side of the vaginal canal wall retractor is open to define a housing free vaginal canal wall retractor, wherein no housing structure surrounds the mirror.

\* \* \* \* \*